United States Patent [19]

Schweigerling

[11] Patent Number: 5,007,914
[45] Date of Patent: Apr. 16, 1991

[54] CATHETER-INSERTION DEVICE

[76] Inventor: Paul E. Schweigerling, 130 Rolling Green La., Elma, N.Y. 14059

[21] Appl. No.: 473,716

[22] Filed: Nov. 15, 1989

Related U.S. Application Data

[62] Division of Ser. No. 208,670, Jun. 20, 1988, Pat. No. 4,889,118.

[51] Int. Cl.⁵ ............................................. A61M 25/01
[52] U.S. Cl. .................................................... 606/108
[58] Field of Search .................. 606/108, 205–207; 128/751–754; 604/164–169, 283, 173; 81/3.8, 318

[56] References Cited

U.S. PATENT DOCUMENTS

| | | |
|---|---|---|
| 611,038 | 9/1898 | Lohman . |
| 2,034,785 | 3/1936 | Wappler ............................ 128/321 |
| 4,435,175 | 3/1984 | Friden ............................... 604/177 |
| 4,478,221 | 10/1984 | Heiss ................................. 128/334 |
| 4,598,699 | 7/1986 | Garren et al. ........................ 128/4 |
| 4,615,472 | 10/1986 | Nash .................................. 226/127 |
| 4,640,274 | 2/1987 | Nakamoto ........................... 128/321 |

FOREIGN PATENT DOCUMENTS 475022 10/1952 Italy ..................................... 128/657

Primary Examiner—C. Fred Rosenbaum
Assistant Examiner—William W. Lewis
Attorney, Agent, or Firm—Joseph P. Gastel

[57] ABSTRACT

A forceps for inserting a catheter into a patient including a pair of jaws for receiving a flange on the neck of a cannula which mounts the catheter, and a catheter-engaging member for engaging the hub of a catheter to force it into the patient, the forceps including finger and thumb-receiving rings connected to the jaws and the catheter-engaging member to cause them to be movable relative to each other to withdraw the cannula from the catheter after the latter has been inserted into the patient.

8 Claims, 4 Drawing Sheets

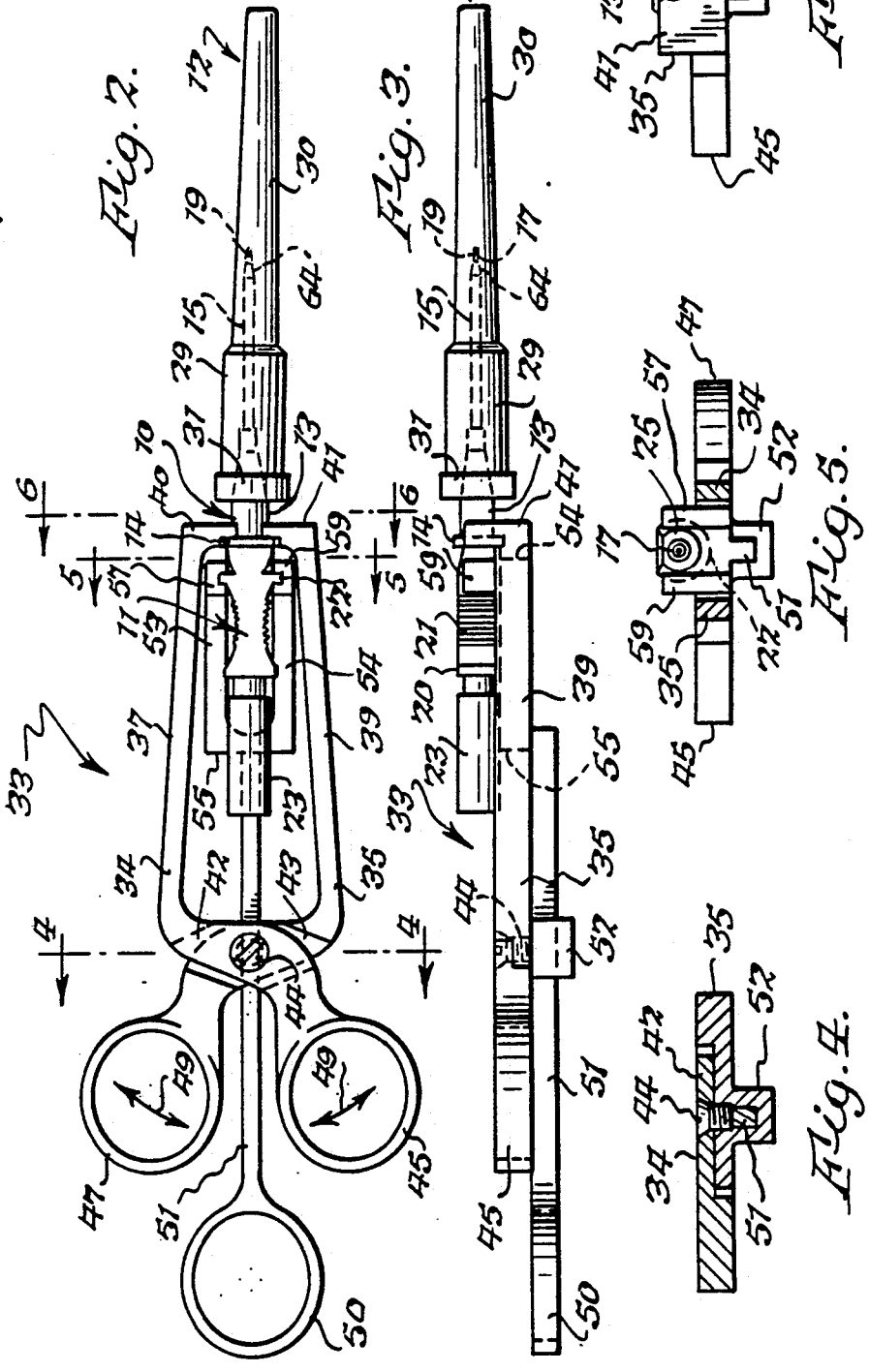

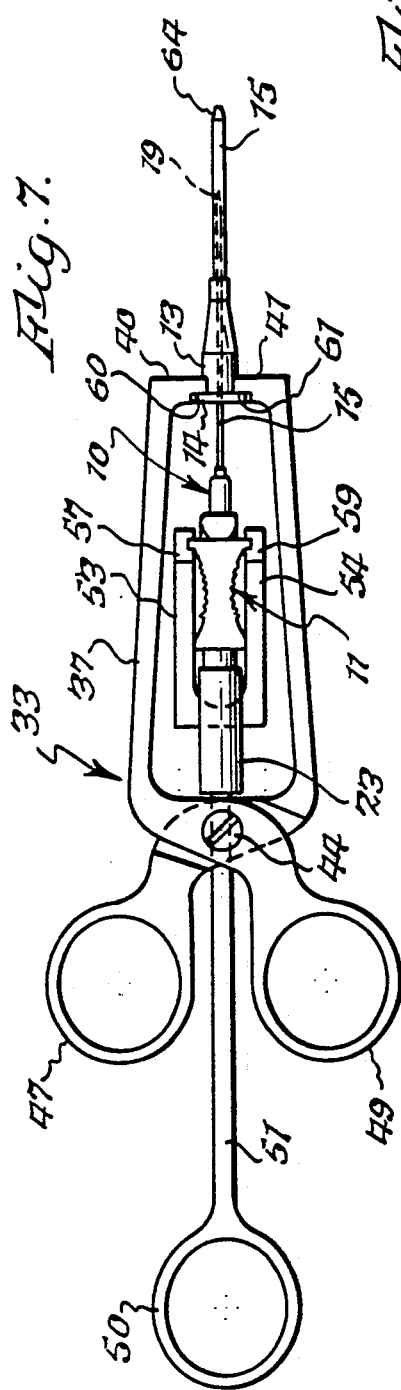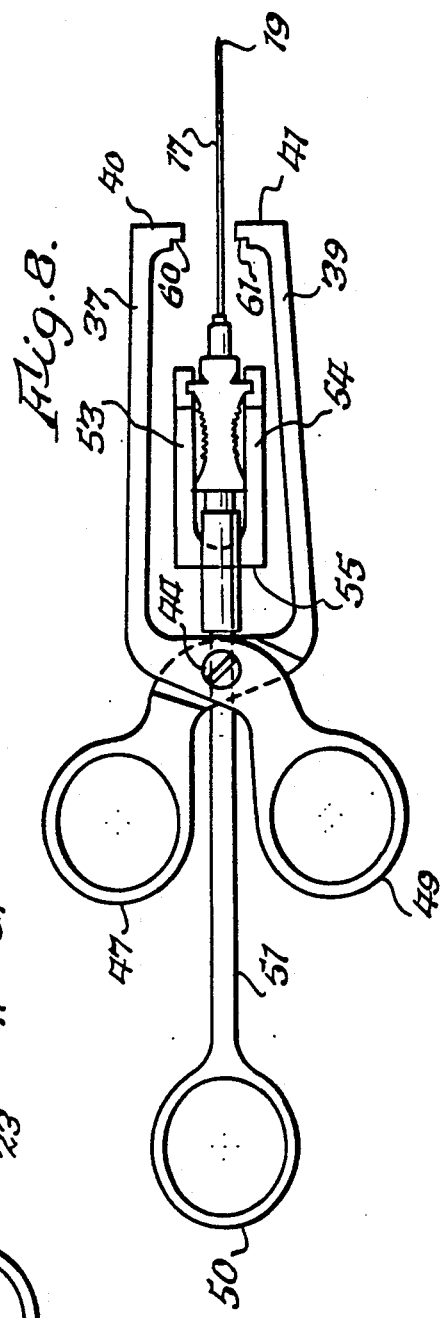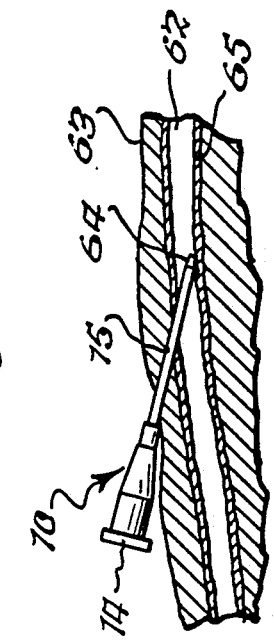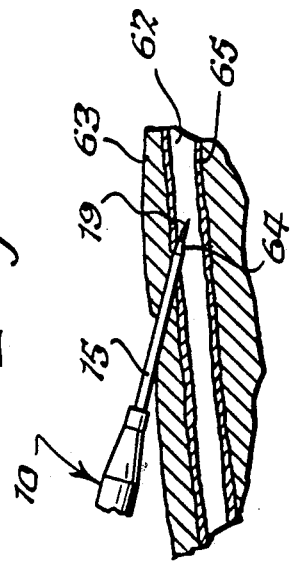

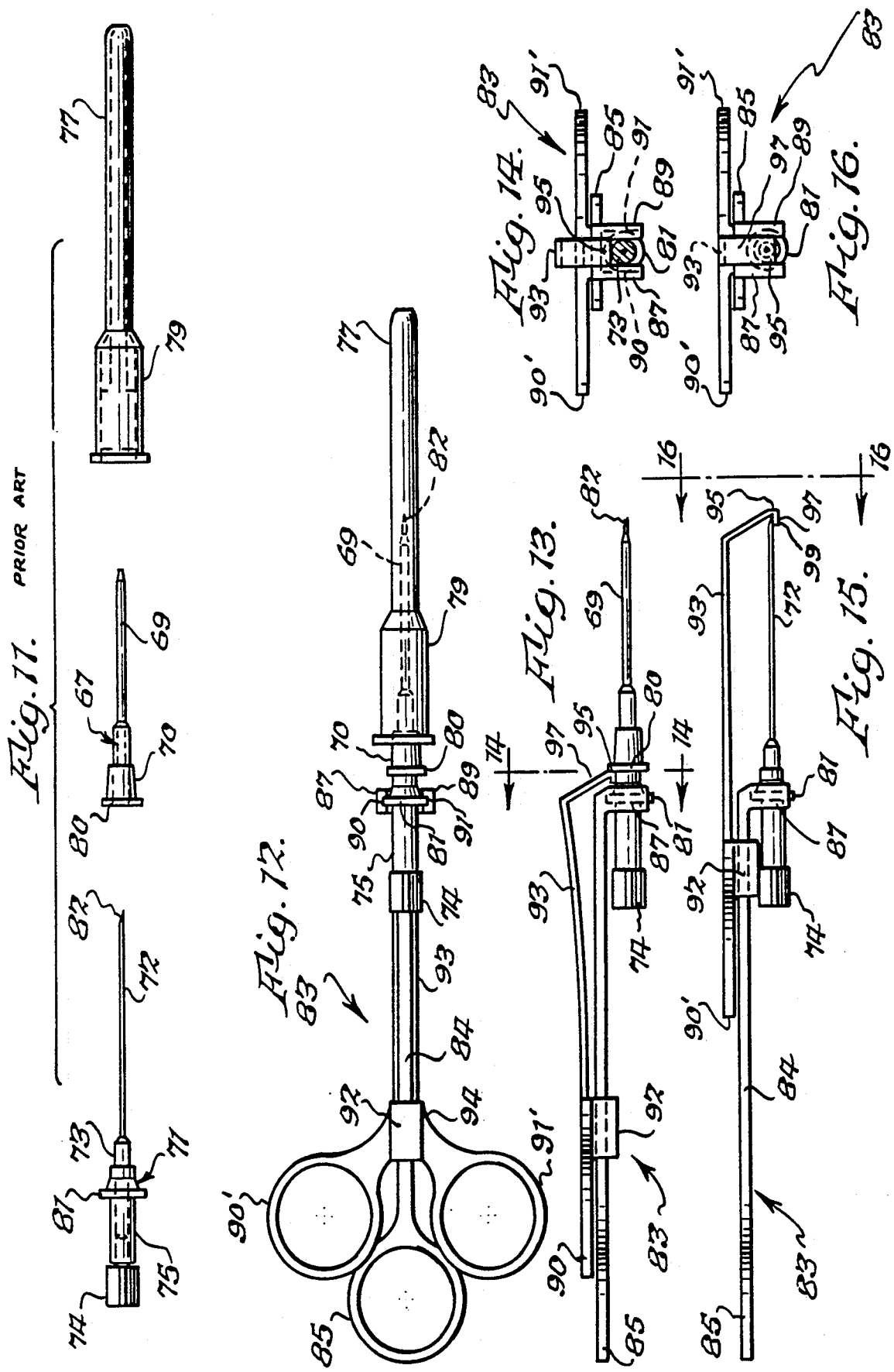

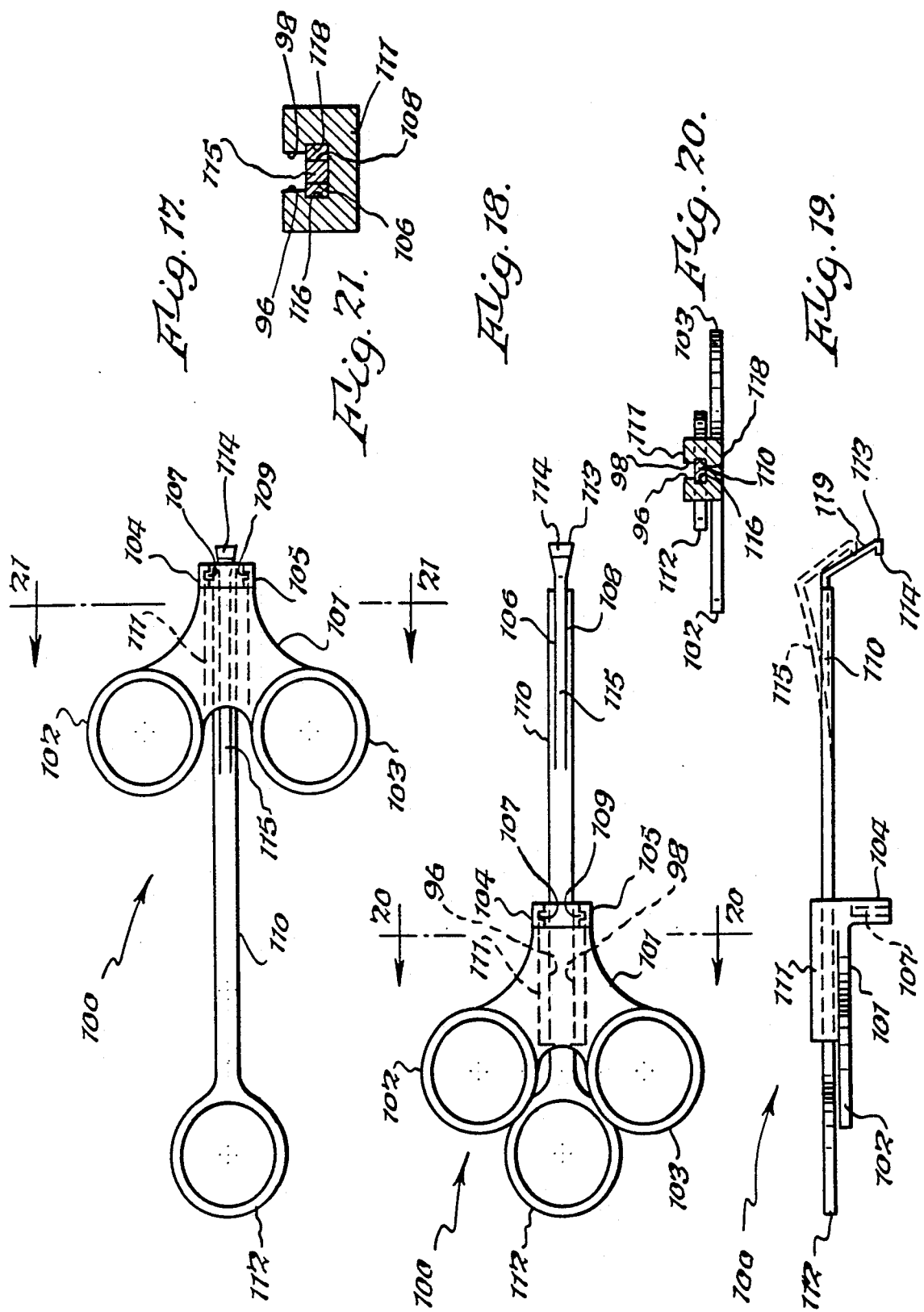

CATHETER-INSERTION DEVICE

This is a division of application Ser. No. 208670 filed June 20, 1988, now U.S. Pat. No. 4,889,118.

BACKGROUND OF THE INVENTION

The present invention relates to a catheter-insertion forceps for inserting in a catheter into a body vessel, such as a vein or artery.

By way of background, there are in use catheter assemblies which comprise a catheter mounted on a cannula with the tip of the needle of the cannula protuding from the end of the catheter. The catheter is inserted into a vein or an artery or other body vessel by forcing the needle which mounts the catheter into the vessel and thereafter withdrawing the needle. This is usually done by manually grasping the hub of the cannula to insert the catheter. However, this causes the person who inserts the catheter to have his hand very close to the patient which could result in the person's hand being sprayed by blood or other body fluid as the needle is withdrawn from the catheter after the latter has been properly placed.

SUMMARY OF THE INVENTION

It is accordingly one object of the present invention to provide a catheter-insertion forceps which permits a cannula-mounted catheter to be inserted into a patient while the user's hand is located remotely from the catheter, thereby avoiding the contamination of the user's hand. Other objects and attendant advantages of the present invention will readily be perceived hereafter.

The present invention relates to a forceps for inserting a catheter into a body vessel of a patient wherein said catheter is of the type having a catheter hub and an elongated tube attached thereto and is mounted on a cannula of the type having a cannula hub with an elongated needle having a pointed tip which extends beyond said tube of said catheter comprising first means for engaging said cannula hub, second means for engaging said catheter hub, first finger-receiving means, first forceps means connecting said first finger-receiving means to said first means, second finger-receiving means, second forceps means connecting said second finger-receiving means to said second means, means mounting said first and second forceps means for movement relative to each other, said first and second means initially occupying a position wherein said cannula and catheter are mounted on said forceps with said pointed tip extending beyond said tube to permit said pointed tip of said cannula and said tube to be initially inserted into said body vessel, and said first and second finger-receiving means being movable relative to each other to withdraw said cannula from said catheter after said tube has been inserted into said body vessel.

The various aspects of the present invention will be more fully understood when the following portions of the specification are read in conjunction with the accompanying drawings wherein:

BRIEF DESCRIPTION OF THE DRAWINGS

FIG. 1 is an exploded view of a cannula with a plug in the end thereof, a catheter which is normally mounted on the cannula and a protective sheath for the assembly;

FIG. 2 is a plan view of a catheter-insertion forceps with the assembled catheter and cannula mounted thereon and with the protective sheath in a position to be removed from the outer ends of the cannula and catheter FIG. 3 is a side elevational view of the assembly of FIG. 2;

FIG. 4 is a cross sectional view taken substantially along line 4—4 of FIG. 2;

FIG. 5 is a cross sectional view taken substantially along line 5—5 of FIG. 2;

FIG. 6 is a cross sectional view taken substantially along line 6—6 of FIG. 2;

FIG. 7 is a view similar to FIG. 2 but showing the cannula withdrawn from the catheter;

FIG. 8 is a view similar to FIG. 7 but showing the catheter released from the forceps;

FIG. 9 is a fragmentary cross sectional schematic view showing the cannula and catheter penetrating the skin and inserted into a vein;

FIG. 10 is a view similar to FIG. 9 but showing the catheter fully inserted into the vein with the cannula withdrawn therefrom;

FIG. 11 is an exploded view of another type of cannula with a plug in the end thereof and with a catheter which is normally mounted on the cannula and a protective sheath for the assembly;

FIG. 12 is a bottom plan view of another embodiment of the catheter insertion forceps with the cannula and catheter of FIG. 11 mounted thereon;

FIG. 13 is a side elevational view of the forceps of FIG. 12 with the parts in the position which they assume when the cannula with the catheter mounted thereon is first inserted into the blood vessel;

FIG. 14 is a cross sectional view taken substantially along line 14—14 of FIG. 13;

FIG. 15 is a side elevational view similar to FIG. 13 but showing the position of the various parts of the forceps after the catheter has been inserted into a blood vessel;

FIG. 16 is an end elevational view taken substantially in the direction of arrows 16—16 of FIG. 15;

FIG. 17 is a plan view of an alternate embodiment of the forceps of FIGS. 12–16 with the parts in the position which they assume prior to the time that the cannula is inserted into a vein;

FIG. 18 is a plan view similar to FIG. 17 but showing the positions of the parts of the forceps after the catheter has been inserted into a vein;

FIG. 19 is a side elevational view of the forceps of FIG. 18;

FIG. 20 is a cross sectional view, which has been inverted, taken substantially along line 20—20 of FIG. 18; and FIG. 21 is an enlarged cross sectional view similar to FIG. 20 but taken along line 21—21 of FIG. 17.

DESCRIPTION OF THE PREFERRED EMBODIMENTS

The purpose of the catheter insertion forceps of the present invention is to permit the insertion of a catheter into a body vessel, such as a vein or artery, with the hand of the person inserting the catheter being remote from the point of penetration of the catheter into the patient to thereby avoid possible contamination of the hand with the blood of the patient.

One form of catheter-cannula assembly is shown in FIG. 1. Normally the catheter 10 is mounted on cannula 11, as shown in FIG. 2 and the ends thereof are protected by a protective sheath 12 having a hub which mounts on the hub of the catheter. The assembled unit is normally provided in a sterile package.

The catheter 10 includes an annular catheter hub 13 having an annular flange 14 at one end thereof and a tube 15 which enters the body vessel. The cannula includes a needle 17 having a beveled end 19. The needle 17 is attached to cannula hub 20 which has a pair of opposite concave faces 21 for receiving fingers of a person. The faces 21 are oriented as shown relative to beveled needle tip 19 to facilitate its insertion into the patient with the bevel oriented upwardly away from the patient. A pair of flanges 22 are located on hub 11 as shown. A removable plug 23 is installed into the hub of cannula 11 to prevent flow of blood or other body fluid from the cannula end when the tip of needle 17 is inserted into a vein or the like.

Normally the catheter 10, cannula 11, and protective sheath 12 are assembled with the cylindrical annular catheter hub portion 13 slidingly received with a mating fit on cylindrical annular cannula hub portion 25 with the side 26 of annular catheter flange 14 abutting face 27 of catheter hub 11. The annular cylindrical hub 29 of protective sheath 12 is normally mounted on catheter hub portion 13 in mating relationship. The tubular end 30 of protective sheath 12 encircles the catheter tube 15 which is mounted on needle 17 as shown in FIG. 2. However, the protective sheath 12 is partially removed in FIG. 2 from its original assembled position wherein the face 31 of flange 32 abuts flange 14 of the catheter.

One embodiment of the catheter insertion forceps of the present invention is shown in FIGS. 2-8. The forceps 33 includes a pair of arms 34 and 35 which include elongated portions 37 and 39, respectively, which have opposed jaws 40 and 41 at their outer ends. Crossover portions 42 and 43 are extensions of portions 37 and 39, respectively, and are pivotally connected to each other by screw 44. Ring-like finger-receiving portions 45 and 47 form extensions of crossover portions 42 and 43, respectively. When finger-receiving portions 45 and 47 are moved in the direction of arrows 49, jaws 40 and 41 may be opened and closed.

A ring-like finger-receiving portion 50 for receiving the thumb of a person is formed at the end of elongated stem 51 which is mounted for rectilinear sliding motion in housing 52 secured to the underside of crossover portion 43 (FIG. 4). A pair of spaced resilient tines 53 and 54 are connected to each other by portion 55 which is secured to the end of stem 51. Spaced slotted jaws 57 and 59 are formed at the end of flexible resilient arms 53 and 54, respectively.

The catheter insertion device of FIGS. 2-8 operates in the following manner: The opposite flanges 22 of cannula hub 11 are slid into slotted jaws 57 and 59 (FIG. 5) of tines 53 and 54, respectively, while the cannula and catheter are assembled as shown in FIGS. 2 and 3. Thereafter, a person's index and middle finger are inserted into ring-like finger-receiving portions 45 and 47 and the fingers are forced together to cause jaws 40 and 41, which were previously more apart, to move toward each other to firmly grasp hub 13 as shown in FIGS. 2 and 3. The flange 14 on hub 13 is received in the recessed portions 60 and 61 (FIG. 8) of jaws 40 and 41, respectively. A person's thumb is inserted into finger-receiving portion 50. Before the foregoing installation of the assembled cannula 11 and catheter 10 is made, the protective sheath 12 is moved from its position on catheter hub 13 to the position shown in FIGS. 2 and 3.

When the person is ready to insert the catheter 10 into a vein or other body vessel 62 (FIGS. 9 and 10), the protective sheath 12 is removed. Thereafter the assembled cannula and catheter, in their positions of FIGS. 2 and 3, are forced through the patient's skin 63. In this respect, the beveled tip 19 of the needle is caused to penetrate skin 63 and vein 62 until the needle point 19 and catheter tube 15 reach the position of FIG. 9. Thereafter, the person's thumb, which is in finger-receiving portion 50, is moved away from his index and middle fingers, which are in finger-receiving portions 47 and 49, until the parts of the forceps 33 reach the position of FIG. 7 wherein needle 17 is withdrawn into catheter tube 15. Thereafter, with the finger-receiving portions 47, 49 and 50 in the position of FIG. 7, the entire forceps 33 is moved toward the patient's skin to move the catheter 10 into the position of FIG. 10. It can thus be seen that the relatively blunt tip 64 of the catheter can be moved into vein 62 without the possibility of sharp needle-tip 19 puncturing the inner portion 65 of the vein.

After the tubular portion 15 of the catheter is inserted into the vein the proper amount, finger-receiving portions 47 and 49 are moved apart to open jaws 40 and 41, as shown in FIG. 8, to thereby release catheter hub 13 and permit needle 17 to be withdrawn in its entirety from catheter 10. Thereafter, a suitable tube can be mounted relative to catheter hub 13.

Another type of catheter and cannula and protective sheath are shown in FIG. 11. The catheter 67 includes a tube 69 and an annular hub 70. The cannula 71 includes a needle 72 and an annular hub 73 onto which catheter hub 70 is mounted. A removable plug 74 is mounted on the end of cannula hub portion 75. A protective sheath 77 includes a hub portion 79 which is mounted on catheter hub 70. An annular flange 80 is located at the end of catheter hub 70, and an annular flange 81 is located on cannula hub 71. A beveled tip 82 is formed at the end of needle 72.

Another embodiment of the catheter-insertion forceps of the present invention is shown in FIGS. 12-16. The catheter-insertion forceps 83 includes a main body portion 84 having a thumb-receiving ring 85 secured to one end thereof and a pair of mirror-image jaws 87 and 89 formed at the opposite end thereof having slots 90 and 91, respectively, for receiving the flange 81 of the cannula. Ring-like finger-receiving portions 90' and 91' for receiving the index and middle finger of a person are rigidly secured to housing 92 which slidably receives member 84. A flexible resilient elongated member 93 has one end fixedly secured to housing 92 at 94 and the other end formed into a combined abutment end 95 and protective cover 97.

The catheter-insertion forceps 83 of FIGS. 12-16 operates in the following manner. The cannula flange 81 is inserted into slotted jaws 87 and 89, as shown in FIG. 12, with the catheter 67, cannula 71, and protective sheath 77 assembled as shown. Prior to insertion of the cannula into sloted jaws 87 and 89, the bevel 82 is positioned so that it will be oriented away from the patient during insertion into the patient. This will cause flexible resilient member 93 to be deflected to the position of FIG. 13 with abutment end 95 thereof in abutting engagement with flange 80 of the catheter. Thereafter, with the person's fingers and thumb in the ring-like members 85, 90' and 91' in the position of FIG. 12, the catheter and cannula are inserted into the vein as described above relative to FIG. 9. Thereafter, with the abutment end 95 against flange 80 of the catheter, the ring-like members 85, 90' and 91' are moved relative to each other by spreading the thumb apart from the fingers to force the catheter tube 15 to the position of FIG. 10. This can be done in either of two ways. The needle 72 can first be withdrawn partially by moving thumb-receiving ring 85 rearwardly and thereafter advancing finger-receiving rings 90 and 91 forwardly, or the reverse can be effected, or the foregoing motions can be performed simultaneously. While the needle 72 is being withdrawn from catheter tube 69, the lower edge 99 of the protective cover 97 will ride along the needle and after the needle is fully withdrawn, the flexibility and resilience of member 93 will cause the protective cover to assume the position shown in FIG. 15 after it passes the tip of the needle, thereby protecting the user of the forceps from being pricked. In order to withdraw the flange 81 from jaws 87 and 89, the protective cover 97 is moved to the right in FIG. 15 and thereafter the flange 81 can be slid out of jaws 87 and 89.

In FIGS. 17-20 an alternate embodiment of the present invention is disclosed which is similar to the embodiment of FIGS. 12-16 except that the catheter insertion process is performed by the relative movement of the index and center fingers toward the thumb, rather than apart as in the embodiment of FIGS. 12-16.

The catheter-insertion forceps 100 of FIGS. 17-19 includes a main body portion 101 to which finger-receiving ring-like members 102 and 103 are rigidly secured. A pair of fixed spaced jaws 104 and 105 are located on the opposite end of body portion 101 from finger-receiving portions 102 and 103. Slots 107 and 109 are formed in jaws 104 and 105, respectively, for receiving flange 81 of the cannula. An elongated stem 110 is slidably received in housing 111 formed at the top of body portion 101. The end of stem 110 is slitted at 106 and 108 so that flexible resilient portion 115 therebetween can deflect upwardly as shown in FIG. 19. Portion 115 is narrower than the spacing between shoulders 96 and 98 of housing 111 so that flexible resilient portion 115 can deflect upwardly in a manner analogous to that shown in FIG. 13 when the parts are in the position of FIG. 17. The sides 116 and 118 of housing 111 guide stem 110 for rectilinear movement. A thumb-receiving ring-like member 112 is formed at the end of flexible resilient member 110 and a combined abutment member 113 and protective cover 114 is formed at the end of flexible resilient member 110. The abutment member 113 is located at the end of portion 119 of protective cover 114.

The embodiment of FIGS. 17-19 operates in essentially the same manner as the embodiment of FIGS. 12-16. As noted above, flange 81 of the cannula is inserted in slots 107 and 109 with the finger-receiving portions 102, 103 and 112 in the position of FIG. 17. In this position, abutment 113 at the end of flexible portion 115 abuts flange 80 of the catheter. The cannula and catheter at this time are in the relative positions shown in FIGS. 12 and 13, and member 115 is deflected in a manner similar to that shown in FIG. 13. Thereafter, with the parts in this position, forceps 100 is moved as a unit until the tip 82 of the needle and the catheter are moved to the position of FIG. 9. Thereafter, thumb-receiving member 12 is advanced toward finger-receiving members 102 and 103 to move the catheter tube 15 to the position of FIG. 10. Alternatively, the finger-receiving portions 102 and 103 can be moved to the left in FIG. 17 to withdraw the tip of the needle into the catheter tube 69. Thereafter the catheter tube can be advanced to the position of FIG. 10 by moving the entire forceps 100 without relative movement between the finger and thumb-receiving rings. Thereafter, the finger-receiving members 102 and 103 are moved to the position of FIGS. 18 and 19 to fully withdraw the needle from the catheter. The protective cover 114 will thus move from its dotted line position of FIG. 19 to its solid line position to shield the end of the needle in the same manner as depicted in FIG. 15.

It can thus be seen that the various embodiments of the catheter-insertion forceps of the present invention are manifestly capable of achieving the above-enumerated objects and while preferred embodiments of the present invention are disclosed, it will be appreciated that it is not limited thereto but may be otherwise embodied within the scope of the following claims.

What is claimed is:

1. A device for inserting a catheter into a body vessel of a patient wherein said catheter is of the type having a catheter hub and an elongated tube attached thereto and is mounted on a cannula of the type having a cannula hub with an elongated needle having a pointed tip which extends into and beyond said tube of said catheter comprising first engagement means for engaging and holding said cannula hub, second engagement means for engaging said catheter hub, first finger-receiving means, first connecting means connecting said first finger-receiving means to said first engagement means, second finger-receiving means, second connecting means connecting said second finger-receiving means to said second engagement means, means mounting said first and second connecting means for movement relative to each other, said first and second engagement means initially occupying a position wherein said cannula and catheter may be cooperatively mounted on said device with said pointed tip extending beyond said tube to permit said pointed tip of said cannula and said tube to be initially inserted into said body vessel, and said first and second finger-receiving means being movable relative to each other while said first engagement means continues to hold said cannula to cause said first engagement means to withdraw said cannula from said catheter after said tube has been inserted into said body vessel and while said second engagement means remains in engagement with said catheter to cause it to remain in position in said body vessel.

2. A device as set forth in claim 1 wherein said second engagement means comprises an abutment member for abutting said catheter hub.

3. A device as set forth in claim 2 wherein said first engagement means comprises a slotted member for receiving a collar on said cannula hub.

4. A device as set forth in claim 2 wherein said means mounting said first and second connecting means relative to each other comprises a slidable connection.

5. A device as set forth in claim 2 wherein said second connecting means comprises an elongated flexible resilient member having an outer end remote from said second finger-receiving means, and wherein said abutment member is located at said outer end.

6. A device as set forth in claim 5 including shielding means at said outer end for shielding said pointed tip of said cannula after said cannula has been withdrawn from said catheter.

7. A device as set forth in claim 6 wherein said flexible resilient member is biased to a first position in a direction away from said cannula when said catheter is mounted on said cannula, and wherein said shielding means is moved to a second position shielding said pointed tip as a result of the resiliency of said flexible resilient member after said cannula has been withdrawn from said catheter.

8. A device as set forth in claim 1 wherein said first and second finger-receiving means are moved together to withdraw said cannula from said catheter.

* * * * *